United States Patent [19]

Isogawa et al.

[11] Patent Number: 5,510,237
[45] Date of Patent: Apr. 23, 1996

[54] SERUM AND PLASMA SEPARATING COMPOSITIONS AND BLOOD TESTING CONTAINERS

[75] Inventors: Hironobu Isogawa, Osaka; Hideo Anraku, Kyoto, both of Japan

[73] Assignee: Sekisui Chemical Co., Ltd., Osaka, Japan

[21] Appl. No.: 391,262

[22] Filed: Feb. 21, 1995

Related U.S. Application Data

[63] Continuation of Ser. No. 888,714, May 27, 1992, abandoned.

[30] Foreign Application Priority Data

Apr. 20, 1992 [JP] Japan ..................... 4-99398

[51] Int. Cl.$^6$ .................. A01N 1/02; C09K 3/00
[52] U.S. Cl. ............. 435/2; 210/516; 210/789; 252/60
[58] Field of Search .............. 435/2; 210/516, 210/789; 252/60; 436/8

[56] References Cited

U.S. PATENT DOCUMENTS 4,994,393  2/1991  Pradhan ................. 436/8

FOREIGN PATENT DOCUMENTS 1-295163   11/1989  Japan.
02095257   4/1990   Japan.

OTHER PUBLICATIONS

Anraku, H., Cyclopentadiene Oligomer Containg . . . Chem AB 113: 2995d 1990.

*Primary Examiner*—Ralph J. Gitomer
*Attorney, Agent, or Firm*—Nikaido, Marmelstein, Murray & Oram

[57] ABSTRACT

The invention provides a serum or plasma separating composition which comprises a cyclopentadiene resin, a viscosity adjusting agent and an organic gelling agent. The composition is characterized in that the cyclopentadiene resin is a liquid resin at a temperature of 25° C., the viscosity adjusting agent being a liquid ester obtained from propionic acid, butyric acid, benzoic acid or phthalic acid, the organic gelling agent being a condensation product of sorbitol and an aromatic aldehyde, the composition containing 0.8 to 25 parts by weight of the viscosity adjusting agent and 0.03 to 0.9 part by weight of the organic gelling agent per 100 parts by weight of the cyclopentadiene resin. The composition forms a satisfactory separating layer even when subjected to a centrifugal separation operation at a set temperature of 4° C.

19 Claims, No Drawings

SERUM AND PLASMA SEPARATING COMPOSITIONS AND BLOOD TESTING CONTAINERS

This application is a continuation of application Ser. No. 07/888,714 Filed May 27, 1992 (now abandoned).

BACKGROUND OF THE INVENTION

The present invention relates to serum or plasma separating compositions for use in centrifuging blood utilizing a difference in specific gravity between blood components, and to blood testing containers having the composition accommodated therein.

Blood testing containers for collecting blood therein are already known which have accommodated in the bottom thereof a serum or plasma separating thixotropic composition such as a mixture of silicone and silica (Unexamined Japanese Patent Publication No. 83654/1976). When blood is collected in the container, allowed to stand for a suitable period of time and thereafter centrifuged, the serum or plasma separating composition, which is in the form of a gel, is fluidized by the centrifugal force. In specific gravity, the gel of the composition is intermediate between the serum or plasma and the clot or cellular (corpuscle) component of the blood, so that the composition gradually rises from the bottom of the container through the collected blood and becomes positioned between a layer of serum or plasma and a layer of blood clot or cells, separating the serum or plasma from the clot or cellular component. The serum or plasma thus separated from the clot or cellular component can be readily withdrawn from the container and subjected to various tests, or can be preserved without being transferred to another container.

The compounds already known for use as the main component of such serum or plasma separating thixotropic compositions include, in addition to the above-mentioned silicone, α-olefin-maleic acid diester copolymer (Unexamined Japanese Patent Publications No. 66956/1981 and No. 168159/1990), polyester polymer (Unexamined Japanese Patent Publication No. 233368/1986), acrylic polymer (Unexamined Japanese Patent Publication No. 42283/1978), chlorinated polybutene (Unexamined Japanese Patent Publication No. 9718/1982), cyclopentadiene resin (Unexamined Japanese Patent Publication No. 295163/1989) and modified cyclopentadiene resin prepared by introducing a hydroxyl, ester, ether, epoxy or like group into cyclopentadiene resin (Unexamined Japanese Patent Publication No. 95257/1990). The materials to be admixed with such a main component as required include, for example, inorganic fillers such as silica, which serve as specific gravity adjusting agents and also as gelling agents for giving thixotropy, substances having a polar group at opposite ends of the molecule, such as propylene glycol and ethylenediamine (such fillers and substances being disclosed in Unexamined Japanese Patent Publication No. 295163/1989), and organic gelling agents such as condensation products of sorbitol and an aromatic aldehyde (Unexamined Japanese Patent Publication No. 168159/1990).

However, silicone forms a phase as distinctly separated from the inorganic filler, undergoes a curing reaction when sterilized by gamma-ray irradiation and is therefore almost out of use presently. α-Olefinmaleic acid diester copolymer, polyester polymer, acrylic polymer, modified cyclopentadiene resin and the like which have a polar group are relatively less likely to affect the determination of substances in the blood under clinical examination, but frequently exert an influence on the measurement of concentration of drugs in the blood (for example, the measurement of concentration of antiepileptics, such as phenobarbital, carbamazepine and phenytoin, in the blood).

On the other hand, the use of chlorinated polybutene entails the problem that when it is to be disposed of by incineration after use, the composition releases hydrochloric acid to cause damage to the incinerator.

Cyclopentadiene resin is superior in that it is free of these drawbacks, but the viscosity of the resin is dependent largely on temperature. Accordingly, it is likely that the serum or plasma separating composition consisting primarily of cyclopentadiene resin will exhibit poor fluidity and fail to function as such composition, for example, when treated for separation in a centrifuge set to a temperature of 4° C. Stated more specifically, the composition consisting primarily of cyclopentadiene resin encounters no problem insofar as it is used approximately at room temperature, i.e., at 20° C. to 25° C., for centrifuging, whereas the composition with the main component of cyclopentadiene resin will not always form a satisfactory separating layer in the case where it is subjected to a centrifugal separation procedure at a temperature of 4° C. using a centrifuge equipped with a refrigerator, as practiced recently to obviate the influence of heat released from the motor of the centrifuge.

To overcome the problem of separation failure, we previously conducted investigations on two-component compositions comprising cyclopentadiene resin and a gelling agent, and found that the composition was unable to exhibit sufficient fluidity when centrifuged at the set temperature of 4° C. (Japanese Patent Application No. 335034/1990)

An object of the present invention is to provide a serum or plasma separating thixotropic composition which comprises a cyclopentadiene resin, a viscosity adjusting agent and an organic gelling agent and which is capable of giving a satisfactory separating layer even when subjected to a centrifugal separation procedure at the set temperature of 4° C., and to provide a blood testing container having the composition accommodated therein.

The methods of sterilizing serum or plasma separating compositions include one wherein the composition is irradiated with gamma rays at a required dose.

The serum or plasma separating composition comprising a cyclopentadiene resin, a viscosity adjusting agent and an organic gelling agent and fulfilling the above object forms a satisfactory separating layer even when subjected to a centrifugal separation procedure at the set temperature of 4° C., exerts no influence on the determination of concentration of drugs in blood and is superior to the conventional serum or plasma separating compositions.

Nevertheless, the composition fulfilling the foregoing object is likely to markedly bubble up when sterilized by gamma-ray irradiation because the composition is decomposed by the irradiation and gasifies. Even when bubbling up and partly decomposed, the composition will not become impaired in its contemplated serum or plasma separating function although this depends on the degree of decomposition, whereas with the lapse of time, the viscosity adjusting agent becomes liable to form a phase separating from the composition. The decomposition due to the gamma-ray irradiation is therefore undesirable.

Another object of the present invention is to provide a serum or plasma separating composition capable of giving a satisfactory separating layer even when subjected to a centrifugal separation procedure at the set temperature of 4° C., producing no influence on the determination of concentration of drugs in blood and having good stability without the likelihood of decomposing and bubbling up even if sterilized by gamma-ray irradiation, and to provide a blood testing container having the composition accommodated therein.

SUMMARY OF THE INVENTION

To accomplish the first object, we have conducted research to find that a composition comprising a specified cyclopentadiene resin, a specified viscosity adjusting agent and a specified organic gelling agent in a suitable ratio affords a satisfactory separating layer even when subjected to a centrifugal separation procedure at the set temperature of 4° C. This finding has matured into the present invention.

To fulfill the second object, we have carried out further research and found that a serum or plasma separating composition giving a satisfactory separating layer, producing no influence on the determination of concentration of drugs in blood and free of the liklihood of decomposing or bubbling up even if irradiated with gamma rays can be prepared by adding a gamma-ray stabilizer to a serum or plasma separating composition comprising a cyclopentadiene resin, a viscosity adjusting agent and an organic gelling agent, the gamma-ray stabilizer being a mixture of a phenolic antioxidant, a photostabilizer and a phosphite antioxidant in a suitable ratio, whereby the present invention has been accomplished.

The present invention provides, as an aspect thereof, a serum or plasma separating composition which fulfills the foregoing first object. This composition comprises a cyclopentadiene resin, a viscosity adjusting agent and an organic gelling agent, the cyclopentadiene resin being a liquid resin at a temperature of 25° C., the viscosity adjusting agent being a liquid ester obtained from propionic acid, butyric acid, benzoic acid or phthalic acid, the organic gelling agent being a condensation product of sorbitol and an aromatic aldehyde, the composition containing 0.8 to 25 parts by weight of the viscosity adjusting agent and 0.03 to 0.9 part by weight of the organic gelling agent per 100 parts by weight of the cyclopentadiene resin.

According to another aspect of the present invention, the foregoing second object can be fulfilled by providing a serum or plasma separating composition which comprises a cyclopentadiene resin, a viscosity adjusting agent, an organic gelling agent and a gamma-ray stabilizer, the cyclopentadiene resin being a liquid resin at a temperature of 25° C., the viscosity adjusting agent being a liquid ester obtained from propionic acid, butyric acid, benzoic acid or phthalic acid, the organic gelling agent being a condensation product of sorbitol and an aromatic aldehyde, the gamma-ray stabilizer being a mixture of a phenolic antioxidant, a photostabilizer and a phosphite antioxidant, the composition containing 0.8 to 25 parts by weight of the viscosity adjusting agent, 0.03 to 0.9 part by weight of the organic gelling agent and 1.32 to 7.7 parts by weight of the gamma-ray stabilizer per 100 parts by weight of the cyclopentadiene resin.

According to a preferred embodiment of composition of the latter type, the phenolic antioxidant is n-octadecyl-3-(4'-hydroxy-3',5'-di-tert-butylphenyl)propionate, the photostabilizer is bis(2,2,6,6-tetramethyl- 4-piperidyl) sebacate and the phosphite antioxidant is 4,4'-butylidene-bis(3-methyl-6-tert-butylphenyl-di-tridecyl)phosphite, the composition containing 0.12 to 0.7 part by weight of the phenolic antioxidant, 0.6 to 3.5 parts by weight of the photostabilizer and 0.6 to 3.5 parts by weight of the phosphite antioxidant per 100 parts by weight of the cyclopentadiene resin.

The present invention further provides a blood testing container having one of these compositions accommodated therein.

The invention has the following advantages.

The serum or plasma separating composition of the invention which comprises a cyclopentadiene resin, a viscosity adjusting agent and an organic gelling agent forms a satisfactory separating layer free of any trouble even when a centrifuge equipped with a refrigerator is used. The composition has almost no polarity, therefore exhibits no hygroscopicity after centrifuging and exerts no adverse effect on the measurement of concentration of drugs in the blood, as well as on the determination of substances in the blood under clinical examination.

The serum or plasma separating composition of the invention which comprises a cyclopentadiene resin, a viscosity adjusting agent, an organic gelling agent and a gamma-ray stabilizer has the remarkable advantage that the composition is unlikely to decompose or bubble up when sterilized by gamma-ray irradiation, in addition to the above advantages.

DETAILED DESCRIPTION OF THE INVENTION

The serum or plasma separating compositions and blood testing containers embodying the invention will be described below in detail.

a) Cyclopentadiene Resin

Cyclopentadiene resin, which is also called DCPD resin or cyclopentadiene petroleum resin, is obtained by thermally dimerizing cyclopentadiene (CPD) present in an amount of 15 to 20% in the $C_5$ fraction of naphtha obtained by cracking. The product of dimerization further contains a co-dimer of cyclopentadiene and isoprene or 1,3-pentadiene. The dimerization followed by de-dimerization and repetitions of distillation affords a product purified to a high degree, i.e., cyclopentadiene resin. This resin is preferably 100 to 300 in number average molecular weight as determined by the polystyrene calibration of the result of gel permeation chromatography because the resin has an increased volatile content if the average molecular weight is too small, or conversely has a high viscosity and is almost solid approximately at room temperature, i.e., at 20° C. to 25° C., if the value is excessively great.

When the cyclopentadiene resin is to be used in the separating composition of the invention, it is desired to saturate the double bond of the resin by hydrogenation since the hydrogenated cyclopentadiene resin is more excellent in heat resistance and weather resistance. In this case, the hydrogenated resin is preferably up to 5.0 (g $Br_2$/100 g) in bromine value as determined by the method prescribed in JIS K2543. If the bromine value is higher, the resin has a stronger offensive odor.

Unlike usual olefinic or α-olefinic polymers, cyclopentadiene resins, which are at least 1.00 in specific gravity, are available relatively easily. Such resins have closely packed polymer molecules, as substantiated by the fact that the resin exhibits little or no evaporation loss at 100° C. Table A shows three examples of preferred cyclopentadiene resins.

TABLE A

Properties of Cyclopentadiene Resins

| Brand name | Manufacturer | Specific gravity | Viscosity (cP) | Av. mol. wt. Mn | Bromine value (g $Br_2$/100 g) |
|---|---|---|---|---|---|
| ECR-327 | Exxon Chemical | 1.040 | 147,000 | 157 | 0.8 |
| Hydrogenated Quintone-1 | Nippon Zeon | 1.030 | 87,000 | 183 | 1.7 |
| Hydrogenated Quintone-2 | Nippon Zeon | 1.030 | 267,000 | 182 | 1.6 |

Specific gravity: Sink-float method using standard copper sulfate solutions for measuring the specific gravity of blood (at about 23° C.).
Viscosity: E-type viscometer, product of Tokyo Keiki Co., Ltd. (3.0°, cone rotor of 14.0 mm in diam., 0.5 r.p.m., 25.0° C.).
Number average molecular weight Mn: GPC (polystyrene calibration).
Bromine value: JIS K 2543 (g $Br_2$/100 g).

Cyclopentadiene resins having such a great specific gravity are easy to prepare, so that those which are intermediate between serum or plasma and blood clot or cells in specific gravity, i.e., those having a specific gravity of about 1.02 to about 1.08, can be easily obtained under selected polymerization conditions. When desired, furthermore, a specific gravity adjusting agent can be admixed with the cyclopentadiene resin for use in the serum or plasma separating composition to thereby adjust the specific gravity of the resin to a desired value. Examples of adjusting agents useful for this purpose are finely divided inorganic materials such as silica, alumina, glass, talc, kaolin, bentonite, titania, zirconium and asbestos, and finely divided organic materials such as polystyrene and polyurethane. The agent is used preferably in an amount of up to 50 parts by weight, more preferably 1 to 10 parts by weight, per 100 parts by weight of the cyclopentadiene resin. When used in too small an amount, the agent fails to serve the function of adjusting specific gravity, whereas presence of an excess of the agent is undesirable since the mixture is then liable to separate into the resin and the agent owing to a great difference therebetween in specific gravity. Moreover, the finely divided material, when added, generally imparts thixotropy to the mixture. The finely divided material is preferably up to 500 μm in mean particle size so as to be mixed with and dispersed in the resin with ease regardless of whether it is inorganic or organic.

On the other hand, cyclopentadiene resins have the nature of exhibiting a greatly increased viscosity with decreasing temperature. More specifically, the cyclopentadiene resin produces no problem insofar as it is used at a temperature of about 20° C. to about 25° C., whereas the serum or plasma separating composition consisting primarily of the resin generally fails to exhibit satisfactory invertibility, for example, when used for separation with a centrifuge set to a temperature of 4° C. To assure the separating composition has improved invertibility at low temperatures, therefore, there is a need to lower the viscosity of the composition at low temperatures.

The term "invertibility" refers to such nature of the serum or plasma separating composition that when blood is collected in a tube or container having the composition accommodated in its bottom and thereafter centrifuged for separation, the composition is fluidized by centrifuging and becomes positioned between a layer of serum or plasma and a layer of blood clot or cells.

b) Viscosity Adjusting Agent

We have conducted extensive research and found that when a blood testing container containing a serum or plasma separating composition at a temperature of about 23° C. is set in a centrifuge adjusted to a temperature of 4° C. and is subjected to a centrifugal separating operation at 1300 G for 5 minutes, the temperature of the composition in the container drops only to 15° C. at the lowest. This indicates that if the separating composition is given the ability to form a satisfactory separating layer or partition at 15° C., the composition exhibits desired invertibility under the centrifugal condition involving the temperature setting of 4° C. Further research conducted has revealed that it is desirable to adjust the separating composition to a viscosity of up to 1,000,000 centipoises (cP) at 15° C.

We have found that the separating composition meeting the above viscosity requirement can be obtained according to the invention by admixing with the cycopentadiene resin a liquid substance serving as a viscosity adjusting agent and having a viscosity of up to 1000 cP, preferably up to 100 cP, at a temperature of 25° C. and a solidifying point of up to 0° C., preferably up to −10° C., so as to give the composition a viscosity of up to 1,000,000 cP at 15° C. Stated more specifically, the viscosity adjusting agent to be used is an ester prepared by reacting an alcohol with propionic acid, butyric acid, benzoic acid or phthalic acid. The alcohol is not limited specifically. Examples of useful alcohols are alkyl alcohols having 1 to 12 carbon atoms, such as methyl alcohol, ethyl alcohol, propyl alcohol, butyl alcohol, isopentyl alcohol, hexyl alcohol, octyl alcohol, 2-ethylhexyl alcohol, nonyl alcohol, decyl alcohol, undecyl alcohol and dodecyl alcohol. These alcohols may be used singly, or at least two of them may be used in combination. In the case of phthalic acid esters, preferable are those obtained from alcohols having a large number of carbon atoms, i.e., 8 to 12 carbon atoms. Especially preferable is an ester obtained with use of a mixture of alcohols having a high straight-chain ratio with 9 to 12 carbon atoms since this ester is highly compatible with the cyclopentadiene resin and less likely to form a separated phase. An example of such an ester is a product of Mitsubishi Gas Chemical Co., Ltd. with the brand name "PL-200." PL-200 is a phthalic acid ester prepared by reacting phthalic anhydride with an alcohol mixture which is a product of Shell Chemical Co., Ltd. with the brand name "Linevol 911" (with a carbon distribution of 20 wt. % $C_9$, 45 wt. % $C_{10}$ and 35 wt. % $C_{11}$, and a total alcohol straight-chain ratio of 80 to 85%). Especially desirable viscosity adjusting agents are PL-200 mentioned above, di(ethylhexyl) phthalate, isopentyl propionate, isopentyl butyrate and butyl benzoate.

The viscosity adjusting agent is used preferably in an amount of 0.8 to 25 parts by weight, more preferably 3 to 20 parts by weight, per 100 parts by weight of the cyclopentadiene resin. If the amount is too small a viscosity reducing effect is not expectable, but conversely, presence of an excess of the agent permits phase separation and is undesirable.

c) Organic Gelling Agent

The organic gelling agent serves as an auxiliary agent for imparting thioxotropy to the composition. The organic gelling agent to be used is a condensation product of sorbitol and an aromatic aldehyde as disclosed in Unexamined Japanese Patent Publication No. 168159/1990. Examples of such condensation products are dibenzylidene sorbitol, tribenzylidene sorbitol, methyl-substituted dibenzylidene sorbitol and the like, among which dibenzylidene sorbitol is especially preferable.

The organic gelling agent in the form of a condensation product of sorbitol and an aromatic aldehyde has the following outstanding advantages.

This type of organic gelling agent has no hygroscopicity or solubility in water, therefore will not permit the separating composition to absorb water and exhibit white turbidity even when the composition is held in contact with a blood sample for a long period of time and does not cause concentration of the sample. Additionally, the gelling agent is compatible with both hydrophobic substances and hydrophilic substances and not susceptible to phase separation since the agent has benzyl as a hydrophobic group and hydroxyl as a hydrophilic group. For the organic gelling agent to exhibit satisfactory thixotropy, it is desired that the agent be dispersed in a hydrophobic medium which is free from polar groups or reduced in polar group content. Furthermore, the gelling agent shows thixotropy more effectively when in combination with the cyclopentadiene resin than when present conjointly with the α-olefin-maleic acid diester copolymer disclosed in Unexamined Japanese Patent Publication No. 168159/1990. This serves to decrease the amount of the gelling agent to be added to the cyclopentadiene resin, consequently allowing the resin to retain its original advantage that it exerts no influence on the measurement of concentration of drugs in the blood. Incidentally, already known as organic gelling agents are substances, such as propylene glycol and ethylenediamine, which have a polar group at opposite ends of the molecule as disclosed in Unexamined Japanese Patent Publication No. 295163/1989, whereas these substances are soluble in water and accordingly have the problem of causing the separating composition to absorb water and concentrate the blood when held in contact with the sample for a long period of time.

The organic gelling agent can be dispersed in another component of the composition when melted by heating, or alternatively when prepared in the form of a solution. In the latter case, the agent is dissolved, for example, at 25° C. in a suitable solvent, e.g. a polar solvent such as dimethyl sulfoxide, N-methylpyrrolidone, N,N-dimethylacetamide, cyclohexanone, N,N-dimethylformamide, hexamethylphosphotriamide or cellosolve solvent in an amount of 5 to 30 parts by weight per 100 parts by weight of the solvent, and the solution is added to the component. When thus dispersed in the component and made compatible therewith, the agent is less susceptible to phase separation.

The organic gelling agent is used preferably in an amount of 0.03 to 0.9 part by weight, more preferably 0.04 to 0.4 part by weight, per 100 parts by weight of the cyclopentadiene resin. If used in too small an amount, the agent fails to give sufficient thixotropy, with the result that the composition is fluidized by a small force other than the centrifugal separating force and becomes difficult to handle. Conversely, an excess of the agent affords excessive thixotropy, such that the present composition becomes unable to shift to a position between the serum or plasma layer and the blood clot or cell layer when subjected to the usual centrifugal separation condition.

d) Gamma-Ray Stabilizer

The gamma-ray stabilizer is a mixture comprising a phenolic antioxidant, a photostabilizer and a phosphite antioxidant.

Typical of phenolic antioxidants is, for example, n-octadecyl-3-(4'-hydroxy-3',5'-di-tertbutylphenyl)propionate. Typical of photostabilizers is, for example, bis(2,2,6,6-tetramethyl-4-piperidyl)sebacate. Typical of phosphite antioxidants is, for example, 4,4'-butylidene-bis(3-methyl-6-tert-butyl-phenyl-di-tridecyl)phosphite.

Examples of substances for use as gamma-ray stabilizers are given in Tables B-1, B-2 and B-3.

TABLE B-1

| Phenolic Antioxidants (Products of Asahi Denka Kogyo K.K.) | |
| --- | --- |
| Brand name | Compound |
| ADK STAB AO-20 | 1,3,5-Tris(3',5'-di-tert-butyl-4'-hydroxybenzyl)-S-triazine-2,4,6(1H,3H,5H)-trione |
| ADK STAB AO-30 | 1,1,3-Tris(2-methyl-4-hydroxy-5-tert-butylphenyl)butane |
| ADK STAB AO-40 | 4,4'-Butylidenebis(3-methyl-6-tert-butylphenol) |
| ADK STAB AO-50 | n-Octadecyl-3-(4'-hydroxy-3',5'-di-tert-butylphenyl) propionate |
| ADK STAB AO-60 | Tetrakis[methylene-3-(3',5'-di-tert-butyl-4-hydroxyphenyl)-propionate]methane |
| ADK STAB AO-75 | 2,2-Thio-diethylenebis[3-(3,5-di-tert-butyl-4-hydroxyphenyl)] propionate |
| ADK STAB AO-80 | 3,9-Bis[1,1-dimethyl-2{β-(3-tert-butyl-4-hydroxy-5-methylphenyl)-propionyloxy}ethyl]-2,4,8,10-tetraoxaspiro[5.5]undecane |
| ADK STAB AO-330 | 1,3,5-Trimethyl-2,4,6-tris(3,5-di-tert-butyl-4-hydroxybenzyl)-benzene |

TABLE B-2

Photostabilizers (Products of Asahi Denka Kogyo K.K.)

| Brand name | Compound |
| --- | --- |
| ADK STAB LA-62 | Condensate of 1,2,3,4-butanetetracarboxylic acid, 1,2,2,6,6-pentamethyl-4-piperidinol and tridecyl alcohol |
| ADK STAB LA-67 | Condensate of 1,2,3,4-butanetetracarboxylic acid, 2,2,6,6-tetramethyl-4-piperidinol and tridecyl alcohol |
| ADK STAB LA-63 | Condensate of 1,2,3,4-butanetetracarboxylic acid, 1,2,2,6,6-pentamethyl-4-piperidinol and β,β,β',β'-tetramethyl-3,9-(2,4,8,10-tetraoxaspiro[5,5]undecane) diethanol |
| ADK STAB LA-68 | Condensate of 1,2,3,4-butanetetracarboxylic acid, 2,2,6,6-tetramethyl-4-piperidinol and β,β,β',β'-tetramethyl-3,9-(2,4,8,10-tetraoxaspiro[5,5]undecane) diethanol |
| ADK STAB LA-77 | Bis(2,2,6,6-tetramethyl-4-piperidyl) sebacate |
| ADK STAB LA-82 | 1,2,2,6,6-Pentamethyl-4-piperidyl methacrylate |
| ADK STAB LA-87 | 2,2,6,6-Tetramethyl-4-piperidyl methacrylate |
| ADK STAB LA-31 | 2,2-Methylenebis[4-(1,1,3,3-tetramethylbutyl)-6-(2H-benzotriazol-2-yl)phenol] |
| ADK STAB LA-32 | 2(2'-Hydroxy-5'-methylphenyl)benzotriazole |
| ADK STAB LA-36 | 2(2'-Hydroxy-3'-tert-butyl-5'-methylphenyl)-5-chlorobenzotriazole |
| ADK STAB 1413 | 2-Hydroxy-4-n-octoxybenzophenone |
| ADK STAB LA-51 | Bis(5-benzoyl-4-hydroxy-2-methoxyphenyl)methane |
| ADK STAB LA-52 | Tetrakis(1,2,2,6,6-pentamethyl-4-piperidyl) 1,2,3,4-butanetetracarboxylate |
| ADK STAB LA-57 | Tetrakis(2,2,6,6-tetramethyl-4-piperidyl) 1,2,3,4-butanetetracarboxylate |

TABLE B-3

Phosphite Antioxidants (Products of Asahi Denka Kogyo K.K.)

| Brand name | Compound |
| --- | --- |
| ADK STAB PEP-24 | Cyclic neopentanetetraylbis(2,4-di-tert-butylphenylphosphite) |
| ADK STAB PEP-8 | Cyclic neopentanetetraylbis(octadecylphosphite) |
| ADK STAB PEP-4C | Cyclic neopentanetetraylbis(nonylphenylphosphite) |
| ADK STAB 2112 | Tris(2,4-di-tert-butylphenylphosphite) |
| ADK STAB 522A | 1,1,3-Tris(2-methyl-4-di-tridecylphosphite-5-tert-butylphenyl)butane |
| ADK STAB 260 | 4,4'-Butylidenebis(3-methyl-6-tert-butylphenyl-di-tridecyl) phosphite |
| ADK STAB 329K | Tris(mixed, mono- and di-nonylphenyl) phosphite |
| ADK STAB 1178 | Tris(nonylphenyl) phosphite |
| ADK STAB 1500 | 4,4'-isopropylidene-diphenolalkyl($C_{12}$–$C_{15}$) phosphite |
| ADK STAB C | Diphenylisooctyl phosphite |
| ADK STAB 135A | Diphenylisodecyl phosphite |
| ADK STAB 517 | Phenyldiisodecyl phosphite |
| ADK STAB 3010 | Trisisodecyl phosphite |
| ADK STAB PEP-36 | Bis(2,6-di-tert-butyl-4-methylphenyl)pentaerythritol-diphosphite |
| ADK STAB HP-10 | 2,2-Methylenebis(4,6-di-tert-butylphenyl)octyl phosphite |

To incorporate the gamma-ray stabilizer to the serum or plasma separating composition comprising a cyclopentadiene resin, viscosity adjusting agent and organic gelling agent, the stabilizer may be added as it is to the mixture of cyclopentadiene resin, viscosity adjusting agent and organic gelling agent. However, the stabilizer can be added in a larger amount when it is used as dissolved in N-methylpyrrolidone, dimethyl sulfoxide or like polar solvent than when the stabilizer is added as it is. This readily affords a serum or plasma separating composition wherein the gamma-ray stabilizer is dispersed satisfactorily.

The phenolic antioxidant of the gamma-ray stabilizer is used preferably in an amount of 0.12 to 0.7 part by weight, more preferably 0.17 to 0.7 part by weight, per 100 parts by weight of the cyclopentadiene resin. The photostabilizer of the gamma-ray stabilizer is used preferably in an amount of 0.6 to 3.5 parts by weight, more preferably 0.8 to 3.5 parts by weight, per 100 parts by weight of the resin. Similarly, the phosphite antioxidant of the gamma-ray stabilizer is used preferably in an amount of 0.6 to 3.5 parts by weight, more preferably 0.8 to 3.5 parts by weight.

If the amounts of the three components of the gamma-ray stabilizer are too small, it is likely that the composition will be decomposed by irradiation with gamma rays to bubble. Conversely, presence of the three components in excessive amounts is not desirable since the polar.solvent used for the purpose of assisting in dispersing these components then permits the composition to absorb water to concentrate the test sample.

The gamma-ray stabilizer acts through the following mechanism. The stabilizer captures radical and like intermediate products of decomposition produced in the separating composition by gamma-ray irradiation, preventing further decomposition of the intermediates.

e) Container

The serum or plasma separating composition embodying the present invention is used generally as accommodated in a container having a bottom and serving as a blood collecting tube of the vacuum type or non-vaccum type for blood testing. When blood is collected in the container by a specified method, then allowed to stand for a suitable period of time and thereafter centrifuged for separation, the blood separates into the serum or plasma, and the clot or cellular component of the blood owing to a difference in specific gravity therebetween, such that in the case where the composition is adjusted to a specific gravity between 1.02 and 1.08, the composition is positioned between the serum or plasma layer in an upper position and the blood clot or cell layer in a lower position, thus serving as a partition therebetween to perform the function of separating composition. The material of the blood testing container to be used can be, for example, a glass or plastics and is not limited specifically.

The amount of the composition of the invention to be contained in the blood testing container made of a glass or plastic, depending on the capacity and shape of the container, is generally 0.3 to 3.0 g per one container.

According to the invention, the blood testing container can be prepared from a thermoplastic resin, thermosetting resin, modified natural resin, glass or the like. Examples of useful thermoplastic resins are polyethylene, polypropylene, poly-4-methylpentene-1, polystyrene, polymethyl methacrylate, polyvinyl chloride, polyethylene terephthalate, polybutylene terephthalate, acrylonitrile polymer, copolymer of an acrylonitrile monomer and styrene, butadiene or the like, styrenebutadiene copolymer, styrene-isoprene copolymer, styrenemaleic anhydride copolymer, styrene-acrylic acid copolymer, styrene-methyl methacrylate copolymer, ethylene-propylene copolymer, ethylene-acrylic acid copolymer, ethylene-acrylate copolymer, acetalized polyvinyl alcohol, polyvinyl alcohol as converted to a butyral, etc. Examples of useful thermosetting resins are unsaturated polyester resin, epoxy resin, epoxyacrylate resin, etc. Examples of useful modified natural resins are cellulose acetate, cellulose propionate, cellulose acetate butyrate, ethyl cellulose, ethyl chitin, etc.

Examples of preferred glasses are soda-lime glass, phosphosilicate glass, borosilicate glass and like silicate glass, silica glass, etc.

EXAMPLES

The present invention will be described with reference to Examples and Comparative Examples given below. The compositions obtained were tested for the evaluation of properties.

Examples 1-1 to 1-14, 2-1 to 2-14, 3-1 to 3-14, 4-1 to 4-14, 5-1 to 5-5, 6-1 to 6-2 and 7-1 to 7-8, and Comparative Examples 1-1 to 1-4, 2-1 to 2-4, 3-1 to 3-4, 4-1 to 4-4, 8-1 to 8-4 and 9-1. to 9-4

Used as hydrogenated cyclopentadiene resins were ECR-327 (brand name), product of Exxon Chemical. Co., Ltd., hydrogenated Quintone-1 and Hydrogenated Quintone-2 (Brand names), products of Nippon Zeon Co., Ltd., having the properties shown in Table A. Used as viscosity adjusting agents were phthalic acid ester A (di(2-ethylhexyl)phthalate), phthalic acid ester B (PL-200 (brand name,)product of Mitsubishi Gas Chemical Co., Inc.), isopentyl propionate, isopentyl butyrate and butyl benzoate. Used as organic gelling agents were Gelol D, which is dibenzylidene sorbitol manufactured by Shinnihon Rika Co., Ltd. (and which was used as dissolved in dimethyl sulfoxide in the form of 20 wt. % solution), and propylene glycol (in some of the Comparative Examples). The specific gravity adjusting agent used was Aerosil which is finely divided silica manufactured by Nippon Aerosil Co., Ltd. (5 to 20 nm in primary particle size, about 7 nm in mean primary particle size).

The materials selected from among these materials were mixed together in the proportions listed in Tables C-1, -2, -3, -4, -5, -6, -7, -8 or -9 and kneaded in a vacuum for 80 minutes to prepare serum or plasma separating compositions.

The specific gravity and viscosity of the compositions prepared were measured, and the compositions were checked for invertibility and white turbidity due to the absorption of water and were each evaluated after standing as accommodated in a container held in a horizontal position.

The results are listed in Tables D-1, -2, -3, -4, -5, -6, -7, -8 and -9.

The specific gravity was measured by the sinkfloat method in a constant-temperature chamber at about 23° C. using copper sulfate solutions. The viscosity was measured at 15° C. or 25° C. using an E-type viscometer, product of Tokyo-Keiki Co., Ltd., having attached thereto a circulation-type constant-temperature bath, and a conical rotor (3.0°, 14.0 mm in diameter) at a rotational speed of 0.5 r.p.m.

The composition was checked for invertibility and white turbidity due to absorption of water by the following procedure. The composition (1.2 g) was placed into a 10-m borosilicate glass tube commercially available to use the tube as a blood testing container. An 8 ml quantity of fresh human blood was injected into the container and allowed to Stand at room temperature, i.e., around 23° C. After recognizing the completion of coagualation of the blood, the container was allowed to stand at 5° C. for 30 minutes and subjected to a separating operation at 1300 G for 5 minutes using a centrifuge having a refrigerator and set to 15° C. The contents were then observed to determine the invertibility by checking the separating layer formed according to the following criteria.

A: A satisfactory separating layer was formed.
B: Although partly remaining on the tube wall, the composition formed a partition.
C: No partition was formed.

The contents were checked with the unaided eye for white turbidity due to water absorption.

For the evaluation of the composition after standing, a 1.2 g quantity of the composition was similarly placed into a 10-ml commercial borosilicate glass tube to use the tube as a blood testing container. The container was then allowed to stand in a horizontal lying position at 60° C. for 24 hours, and the composition was checked for the resulting mode of flow. If the viscosity adjusting agent separated from the composition, the result was interpreted as "phase separation." When the composition flowed to the tube opening, the result was interpreted as an "excessive flow."

TABLE C-1

(parts by weight)

| Example or Comp. Ex. | Comp. Ex. 1-1 | Ex. 1-1 | Ex. 1-2 | Ex. 1-3 | Ex. 1-4 | Comp. Ex. 1-2 | Comp. Ex. 1-3 | Ex. 1-5 | Ex. 1-6 |
|---|---|---|---|---|---|---|---|---|---|
| Cyclopentadiene resin ECR-327 | 100 | 100 | 100 | 100 | 100 | 100 | 100 | 100 | 100 |
| Viscosity adjusting agent | | | | | | | | | |
| Phthalic acid ester A | 0.5 | 1 | 5 | 10 | 20 | 30 | | | |
| Phthalic acid ester B | | | | | | | 0.5 | 1 | 5 |
| Isopentyl propionate | | | | | | | | | |
| Isopentyl butyrate | | | | | | | | | |
| Butyl benzoate | | | | | | | | | |
| Organic gelling agent | | | | | | | | | |
| Gelol D | 0.08 | 0.08 | 0.08 | 0.08 | 0.08 | 0.08 | 0.08 | 0.08 | 0.08 |
| Propylene glycol | | | | | | | | | |
| Specific gravity adjusting agent | | | | | | | | | |
| Aerosil | 3 | 3 | 3 | 3 | 3 | 3 | 3 | 3 | 3 |

| Example or Comp. Ex. | Ex. 1-7 | Ex. 1-8 | Comp. Ex. 1-4 | Ex. 1-9 | Ex. 1-10 | Ex. 1-11 | Ex. 1-12 | Ex. 1-13 | Ex. 1-14 |
|---|---|---|---|---|---|---|---|---|---|
| Cyclopentadiene resin ECR-327 | 100 | 100 | 100 | 100 | 100 | 100 | 100 | 100 | 100 |
| Viscosity adjusting agent | | | | | | | | | |
| Phthalic acid ester A | | | | | | | | | |
| Phthalic acid ester B | 10 | 20 | 30 | | | | | | |
| Isopentyl propionate | | | | 5 | 10 | | | | |
| Isopentyl butyrate | | | | | | 5 | 10 | | |
| Butyl benzoate | | | | | | | | 5 | 10 |
| Organic gelling agent | | | | | | | | | |
| Gelol D | 0.08 | 0.08 | 0.08 | 0.08 | 0.08 | 0.08 | 0.08 | 0.08 | 0.08 |
| Propylene glycol | | | | | | | | | |
| Specific gravity adjusting agent | | | | | | | | | |
| Aerosil | 3 | 3 | 3 | 3 | 3 | 3 | 3 | 3 | 3 |

TABLE D-1

| Example or Comp. Ex. | Comp. Ex. 1-1 | Ex. 1-1 | Ex. 1-2 | Ex. 1-3 | Ex. 1-4 | Comp. Ex. 1-2 | Comp. Ex. 1-3 | Ex. 1-5 | Ex. 1-6 |
|---|---|---|---|---|---|---|---|---|---|
| Properties | | | | | | | | | |
| Specific gravity (at 23° C. in constant-temperature chamber) | 1.056 | 1.055 | 1.052 | 1.048 | 1.041 | 1.035 | 1.056 | 1.055 | 1.052 |
| Viscosity (E-type viscometer) | | | | | | | | | |
| 15° C. (× 10,000 cP) | >100 | 78.3 | 37.9 | 23.2 | 17.5 | 13.4 | >100 | 79.2 | 36.5 |
| 25° C. (× 10,000 cP) | 16.8 | 13.1 | 11.4 | 8.3 | 7.8 | 6.7 | 17.1 | 13.5 | 12.2 |
| Performance | | | | | | | | | |
| Invertibility (15° C., 1300 G × 5 min) | C | B | A | A | A | A | C | B | A |
| White turbidity | No | No | No | No | No | No | No | No | No |
| Evaluation after standing | Good | Good | Good | Good | Good | PS* | Good | Good | Good |

TABLE D-1-continued

| Example or Comp. Ex. | Ex. 1-7 | Ex. 1-8 | Comp. Ex. 1-4 | Ex. 1-9 | Ex. 1-10 | Ex. 1-11 | Ex. 1-12 | Ex. 1-13 | Ex. 1-14 |
|---|---|---|---|---|---|---|---|---|---|
| Properties | | | | | | | | | |
| Specific gravity (at 23° C. in constant-temperature chamber) | 1.048 | 1.041 | 1.035 | 1.045 | 1.035 | 1.046 | 1.036 | 1.054 | 1.052 |
| Viscosity (E-type viscometer) | | | | | | | | | |
| 15° C. (× 10,000 cP) | 24.1 | 17.3 | 12.8 | 25.2 | 18.6 | 22.5 | 17.6 | 28.7 | 19.3 |
| 25° C. (× 10,000 cP) | 8.1 | 7.6 | 5.9 | 9.1 | 7.0 | 8.7 | 6.2 | 9.2 | 7.1 |
| Performance | | | | | | | | | |
| Invertibility (15° C., 1300 G × 5 min) | A | A | A | A | A | A | A | A | A |
| White turbidity Evaluation after standing | No Good | No Good | No PS* | No Good | No Good | No Good | No Good | No Good | No Good |

*PS stands for phase separation.

TABLE C-2

| | (parts by weight) | | | | | | | | |
|---|---|---|---|---|---|---|---|---|---|
| Example or Comp. Ex. | Comp. Ex. 2-1 | Ex. 2-1 | Ex. 2-2 | Ex. 2-3 | Ex. 2-4 | Comp. Ex. 2-2 | Comp. Ex. 2-3 | Ex. 2-5 | Ex. 2-6 |
| Cyclopentadiene resin ECR-327 | 100 | 100 | 100 | 100 | 100 | 100 | 100 | 100 | 100 |
| Viscosity adjusting agent | | | | | | | | | |
| Phthalic acid ester A | 5 | 5 | 5 | 5 | 5 | 5 | | | |
| Phthalic acid ester B | | | | | | | 5 | 5 | 5 |
| Isopentyl propionate | | | | | | | | | |
| Isopentyl butyrate | | | | | | | | | |
| Butyl benzoate | | | | | | | | | |
| Organic gelling agent | | | | | | | | | |
| Gelol D | 0.02 | 0.04 | 0.08 | 0.2 | 0.5 | 1.0 | 0.02 | 0.04 | 0.08 |
| Propylene glycol | | | | | | | | | |
| Specific gravity adjusting agent | | | | | | | | | |
| Aerosil | 3 | 3 | 3 | 3 | 3 | 3 | 3 | 3 | 3 |

| Example or Comp. Ex. | Ex. 2-7 | Ex. 2-8 | Comp. Ex. 2-4 | Ex. 2-9 | Ex. 2-10 | Ex. 2-11 | Ex. 2-12 | Ex. 2-13 | Ex. 2-14 |
|---|---|---|---|---|---|---|---|---|---|
| Cyclopentadiene resin ECR-327 | 100 | 100 | 100 | 100 | 100 | 100 | 100 | 100 | 100 |
| Viscosity adjusting agent | | | | | | | | | |
| Phthalic acid ester A | | | | | | | | | |
| Phthalic acid ester B | 5 | 5 | 5 | | | | | | |
| Isopentyl propionate | | | | 5 | 5 | | | | |
| Isopentyl butyrate | | | | | | 5 | 5 | | |
| Butyl benzoate | | | | | | | | 5 | 5 |
| Organic gelling agent | | | | | | | | | |
| Gelol D | 0.2 | 0.5 | 1.0 | 0.08 | 0.2 | 0.08 | 0.2 | 0.08 | 0.2 |
| Propylene glycol | | | | | | | | | |
| Specific gravity adjusting agent | | | | | | | | | |
| Aerosil | 3 | 3 | 3 | 3 | 3 | 3 | 3 | 3 | 3 |

TABLE D-2

| Example or Comp. Ex. | Comp. Ex. 2-1 | Ex. 2-1 | Ex. 2-2 | Ex. 2-3 | Ex. 2-4 | Comp. Ex. 2-2 | Comp. Ex. 2-3 | Ex. 2-5 | Ex. 2-6 |
|---|---|---|---|---|---|---|---|---|---|
| Properties | | | | | | | | | |
| Specific gravity (at 23° C. in constant-temperature chamber) | 1.052 | 1.052 | 1.052 | 1.052 | 1.053 | 1.054 | 1.052 | 1.052 | 1.052 |
| Viscosity (E-type viscometer) | | | | | | | | | |
| 15° C. (× 10,000 cP) | 27.1 | 30.5 | 37.9 | 41.3 | 63.7 | >100 | 28.0 | 29.2 | 36.5 |
| 25° C. (× 10,000 cP) | 10.2 | 10.9 | 11.4 | 12.2 | 12.9 | 14.3 | 10.6 | 11.1 | 12.2 |
| Performance | | | | | | | | | |
| Invertibility (15° C., 1300 G × 5 min) | A | A | A | A | B | C | A | A | A |
| White turbidity | No | No | No | No | No | No | No | No | No |
| Evaluation after standing | EF* | Good | Good | Good | Good | Good | EF* | Good | Good |

| Example or Comp. Ex. | Ex. 2-7 | Ex. 2-8 | Comp. Ex. 2-4 | Ex. 2-9 | Ex. 2-10 | Ex. 2-11 | Ex. 2-12 | Ex. 2-13 | Ex. 2-14 |
|---|---|---|---|---|---|---|---|---|---|
| Properties | | | | | | | | | |
| Specific gravity (at 23° C. in constant-temperature chamber) | 1.052 | 1.053 | 1.054 | 1.045 | 1.046 | 1.046 | 1.046 | 1.054 | 1.054 |
| Viscosity (E-type viscometer) | | | | | | | | | |
| 15° C. (× 10,000 cP) | 40.7 | 62.5 | >100 | 25.2 | 35.3 | 22.5 | 30.8 | 28.7 | 32.1 |
| 25° C. (× 10,000 cP) | 13.1 | 13.3 | 15.2 | 9.1 | 10.8 | 8.7 | 10.0 | 9.2 | 11.1 |
| Performance Invertibility (15° C., 1300 G × 5 min) | A | B | C | A | A | A | A | A | A |
| White turbidity | No | No | No | No | No | No | No | No | No |
| Evaluation after standing | Good | Good | Good | Good | Good | Good | Good | Good | Good |

*EF = excessive flow.

TABLE C-3

| | (parts by weight) | | | | | | | | |
|---|---|---|---|---|---|---|---|---|---|
| Example or Comp. Ex. | Comp. Ex. 3-1 | Ex. 3-1 | Ex. 3-2 | Ex. 3-3 | Ex. 3-4 | Comp. Ex. 3-2 | Comp. Ex. 3-3 | Ex. 3-5 | Ex. 3-6 |
| Cyclopentadiene resin | | | | | | | | | |
| Hydrogenated Quintone-1 | 100 | 100 | 100 | 100 | 100 | 100 | 100 | 100 | 100 |
| Viscosity adjusting agent | | | | | | | | | |
| Phthalic acid ester A | 0.5 | 1 | 5 | 10 | 20 | 30 | | | |
| Phthalic acid ester B | | | | | | | 0.5 | 1 | 5 |
| Isopentyl propionate | | | | | | | | | |
| Isopentyl butyrate | | | | | | | | | |
| Butyl benzoate | | | | | | | | | |
| Organic gelling agent | | | | | | | | | |
| Gelol D | 0.08 | 0.08 | 0.08 | 0.08 | 0.08 | 0.08 | 0.08 | 0.08 | 0.08 |
| Propylene glycol | | | | | | | | | |
| Specific gravity adjusting agent | | | | | | | | | |
| Aerosil | 3 | 3 | 3 | 3 | 3 | 3 | 3 | 3 | 3 |

TABLE C-3-continued

| Example or Comp. Ex. | Ex. 3-7 | Ex. 3-8 | Comp. Ex. 3-4 | Ex. 3-9 | Ex. 3-10 | Ex. 3-11 | Ex. 3-12 | Ex. 3-13 | Ex. 3-14 |
|---|---|---|---|---|---|---|---|---|---|
| Cyclopentadiene resin | | | | | | | | | |
| Hydrogenated Quintone-1 | 100 | 100 | 100 | 100 | 100 | 100 | 100 | 100 | 100 |
| Viscosity adjusting agent | | | | | | | | | |
| Phthalic acid ester A | | | | | | | | | |
| Phthalic acid ester B | 10 | 20 | 30 | | | | | | |
| Isopentyl propionate | | | | 5 | 10 | | | | |
| Isopentyl butyrate | | | | | | 5 | 10 | | |
| Butyl benzoate | | | | | | | | 5 | 10 |
| Organic gelling agent | | | | | | | | | |
| Gelol D | 0.08 | 0.08 | 0.08 | 0.08 | 0.08 | 0.08 | 0.08 | 0.08 | 0.08 |
| Propylene glycol | | | | | | | | | |
| Specific gravity adjusting agent | | | | | | | | | |
| Aerosil | 3 | 3 | 3 | 3 | 3 | 3 | 3 | 3 | 3 |

TABLE D-3

| Example or Comp. Ex. | Comp. Ex. 3-1 | Ex. 3-1 | Ex. 3-2 | Ex. 3-3 | Ex. 3-4 | Comp. Ex. 3-2 | Comp. Ex. 3-3 | Ex. 3-5 | Ex. 3-6 |
|---|---|---|---|---|---|---|---|---|---|
| Properties | | | | | | | | | |
| Specific gravity | | | | | | | | | |
| (at 23° C. in constant-temperature chamber) | 1.046 | 1.046 | 1.042 | 1.039 | 1.032 | 1.027 | 1.046 | 1.046 | 1.043 |
| Viscosity (E-type viscometer) | | | | | | | | | |
| 15° C. (× 10,000 cP) | >100 | 46.3 | 22.3 | 13.6 | 10.3 | 7.8 | >100 | 46.8 | 21.7 |
| 25° C. (× 10,000 cP) | 9.9 | 7.9 | 6.6 | 4.9 | 4.6 | 4.1 | 10.1 | 8.1 | 7.1 |
| Performance | | | | | | | | | |
| Invertibility (15° C., 1300 G × 5 min) | C | A | A | A | A | A | C | A | A |
| White turbidity | No | No | No | No | No | No | No | No | No |
| Evaluation after standing | Good | Good | Good | Good | Good | PS* | Good | Good | Good |

| Example or Comp. Ex. | Ex. 3-7 | Ex. 3-8 | Comp. Ex. 3-4 | Ex. 3-9 | Ex. 3-10 | Ex. 3-11 | Ex. 3-12 | Ex. 3-13 | Ex. 3-14 |
|---|---|---|---|---|---|---|---|---|---|
| Properties | | | | | | | | | |
| Specific gravity | | | | | | | | | |
| (at 23° C. in constant-temperature chamber) | 1.039 | 1.033 | 1.028 | 1.036 | 1.027 | 1.036 | 1.028 | 1.044 | 1.043 |
| Viscosity (E-type viscometer) | | | | | | | | | |
| 15° C. (× 10,000 cP) | 14.4 | 10.2 | 7.6 | 14.8 | 11.0 | 13.2 | 10.5 | 17.0 | 11.4 |
| 25° C. (× 10,000 cP) | 4.8 | 4.4 | 3.5 | 5.4 | 4.2 | 5.1 | 3.6 | 5.5 | 4.2 |
| Performance | | | | | | | | | |
| Invertibility (15° C., 1300 G × 5 min) | A | A | A | A | A | A | A | A | A |
| White turbidity | No | No | No | No | No | No | No | No | No |
| Evaluation after standing | Good | Good | PS* | Good | Good | Good | Good | Good | Good |

*PS = phase separation

TABLE C-4

| | (parts by weight) | | | | | | | | |
|---|---|---|---|---|---|---|---|---|---|
| Example or Comp. Ex. | Comp. Ex. 4-1 | Ex. 4-1 | Ex. 4-2 | Ex. 4-3 | Ex. 4-4 | Comp. Ex. 4-2 | Comp. Ex. 4-3 | Ex. 4-5 | Ex. 4-6 |
| Cyclopentadiene resin | | | | | | | | | |
| Hydrogenated Quintone-1 | 100 | 100 | 100 | 100 | 100 | 100 | 100 | 100 | 100 |
| Viscosity adjusting agent | | | | | | | | | |
| Phthalic acid ester A | 5 | 5 | 5 | 5 | 5 | 5 | | | |
| Phthalic acid ester B | | | | | | | 5 | 5 | 5 |
| Isopentyl propionate | | | | | | | | | |
| Isopentyl butyrate | | | | | | | | | |
| Butyl benzoate | | | | | | | | | |
| Organic gelling agent | | | | | | | | | |
| Gelol D | 0.02 | 0.04 | 0.08 | 0.2 | 0.5 | 1.0 | 0.02 | 0.04 | 0.08 |
| Propylene glycol | | | | | | | | | |
| Specific gravity adjusting agent | | | | | | | | | |
| Aerosil | 3 | 3 | 3 | 3 | 3 | 3 | 3 | 3 | 3 |

| Example or Comp. Ex. | Ex. 4-7 | Ex. 4-8 | Comp. Ex. 4-4 | Ex. 4-9 | Ex. 4-10 | Ex. 4-11 | Ex. 4-12 | Ex. 4-13 | Ex. 4-14 |
|---|---|---|---|---|---|---|---|---|---|
| Cyclopentadiene resin | | | | | | | | | |
| Hydrogenated Quintone-1 | 100 | 100 | 100 | 100 | 100 | 100 | 100 | 100 | 100 |
| Viscosity adjusting agent | | | | | | | | | |
| Phthalic acid ester A | | | | | | | | | |
| Phthalic acid ester B | 5 | 5 | 5 | | | | | | |
| Isopentyl propionate | | | | 5 | 5 | | | | |
| Isopentyl butyrate | | | | | | 5 | 5 | | |
| Butyl benzoate | | | | | | | | 5 | 5 |
| Organic gelling agent | | | | | | | | | |
| Gelol D | 0.2 | 0.5 | 1.0 | 0.08 | 0.2 | 0.08 | 0.2 | 0.08 | 0.2 |
| Propylene glycol | | | | | | | | | |
| Specific gravity adjusting agent | | | | | | | | | |
| Aerosil | 3 | 3 | 3 | 3 | 3 | 3 | 3 | 3 | 3 |

TABLE D-4

| Example or Comp. Ex. | Comp. Ex. 4-1 | Ex. 4-1 | Ex. 4-2 | Ex. 4-3 | Ex. 4-4 | Comp. Ex. 4-2 | Comp. Ex. 4-3 | Ex. 4-5 | Ex. 4-6 |
|---|---|---|---|---|---|---|---|---|---|
| Properties | | | | | | | | | |
| Specific gravity | | | | | | | | | |
| (at 23° C. in constant-temperature chamber) | 1.042 | 1.042 | 1.042 | 1.043 | 1.043 | 1.045 | 1.042 | 1.042 | 1.043 |
| Viscosity (E-type viscometer) | | | | | | | | | |
| 15° C. (× 10,000 cP) | 15.9 | 18.1 | 22.3 | 24.5 | 37.7 | >100 | 16.6 | 17.4 | 21.5 |
| 25° C. (× 10,000 cP) | 6.0 | 6.4 | 6.7 | 7.1 | 7.5 | 8.5 | 6.4 | 6.7 | 7.2 |
| Performance | | | | | | | | | |
| Invertibility (15° C., 1300 G × 5 min) | A | A | A | A | A | C | A | A | A |
| White turbidity | No | No | No | No | No | No | No | No | No |
| Evaluation after standing | EF* | Good | Good | Good | Good | Good | EF* | Good | Good |

TABLE D-4-continued

| Example or Comp. Ex. | Ex. 4-7 | Ex. 4-8 | Comp. Ex. 4-4 | Ex. 4-9 | Ex. 4-10 | Ex. 4-11 | Ex. 4-12 | Ex. 4-13 | Ex. 4-14 |
|---|---|---|---|---|---|---|---|---|---|
| Properties | | | | | | | | | |
| Specific gravity | | | | | | | | | |
| (at 23° C. in constant-temperature chamber) | 1.043 | 1.044 | 1.045 | 1.036 | 1.036 | 1.036 | 1.037 | 1.044 | 1.045 |
| Viscosity (E-type viscometer) | | | | | | | | | |
| 15° C. (× 10,000 cP) | 24.1 | 37.0 | >100 | 14.8 | 20.9 | 13.4 | 18.3 | 17.0 | 18.9 |
| 25° C. (× 10,000 cP) | 7.8 | 7.9 | 9.0 | 5.3 | 6.5 | 5.1 | 5.9 | 5.4 | 6.7 |
| Performance | | | | | | | | | |
| Invertibility (15° C., 1300 G × 5 min) | A | A | C | A | A | A | A | A | A |
| White turbidity | No | No | No | No | No | No | No | No | No |
| Evaluation after standing | Good | Good | Good | Good | Good | Good | Good | Good | Good |

*EF = excessive flow

TABLE C-5

| | (parts by weight) | | | | |
|---|---|---|---|---|---|
| Example | 5-1 | 5-2 | 5-3 | 5-4 | 5-5 |
| Cyclopentadiene resin | | | | | |
| Hydrogenated Quintone-2 | 100 | 100 | 100 | 100 | 100 |
| Viscosity adjusting agent | | | | | |
| Phthalic acid ester A | 10 | | | | |
| Phthalic acid ester B | | 10 | | | |
| Isopentyl propionate | | | 10 | | |
| Isopentyl butyrate | | | | 10 | |
| Butyl benzoate | | | | | 10 |
| Organic gelling agent | | | | | |
| Gelol D | 0.08 | 0.08 | 0.08 | 0.08 | 0.08 |
| Propylene glycol | | | | | |
| Specific gravity adjusting agent | | | | | |
| Aerosil | 3 | 3 | 3 | 3 | 3 |

TABLE D-5

| Example | 5-1 | 5-2 | 5-3 | 5-4 | 5-4 |
|---|---|---|---|---|---|
| Properties | | | | | |
| Specific gravity | | | | | |
| (at 23° C. in constant-temperature chamber) | 1.039 | 1.039 | 1.027 | 1.028 | 1.043 |
| Viscosity (E-type viscometer) | | | | | |
| 15° C. (× 10,000 cP) | 42.1 | 43.8 | 33.9 | 32.0 | 35.2 |
| 25° C. (× 10,000 cP) | 15.2 | 14.8 | 12.6 | 11.2 | 12.8 |
| Performance | | | | | |
| Invertibility (15° C., 1300 G × 5 min) | A | A | A | A | A |
| White turbidity | No | No | No | No | No |
| Evaluation after standing | Good | Good | Good | Good | Good |

TABLE C-6

| | (parts by weight) | |
|---|---|---|
| Example | 6-1 | 6-2 |
| Cyclopentadiene resin | | |
| Hydrogenated Quintone-2 | 100 | 100 |
| Viscosity adjusting agent | | |
| Phthalic acid ester A | 5 | |
| Phthalic acid ester B | | 5 |
| Isopentyl propionate | | |
| Isopentyl butyrate | | |
| Butyl benzoate | | |
| Organic gelling agent | | |
| Gelol D | 0.04 | 0.04 |
| Propylene glycol | | |
| Specific gravity adjusting agent | | |
| Aerosil | 3 | 3 |

TABLE D-6

| Example | 6-1 | 6-2 |
|---|---|---|
| Properties | | |
| Specific gravity | | |
| (at 23° C. in constant-temperature chamber) | 1.042 | 1.042 |
| Viscosity (E-type viscometer) | | |
| 15° C. (× 10,000 cP) | 55.3 | 52.9 |
| 25° C. (× 10,000 cP) | 19.7 | 20.3 |
| Performance | | |
| Invertibility (15° C., 1300 G × 5 min) | A | A |
| White turbidity | No | No |
| Evaluation after standing | Good | Good |

TABLE C-7

| Example | 7-1 | 7-2 | 7-3 | 7-4 | 7-5 | 7-6 | 7-7 | 7-8 |
|---|---|---|---|---|---|---|---|---|
| (parts by weight) | | | | | | | | |
| Cyclopentadiene resin | | | | | | | | |
| ECR-327 | 100 | 100 | 100 | 100 | 100 | 100 | 100 | 100 |
| Viscosity adjusting agent | | | | | | | | |
| Phthalic acid ester A | 2 | 10 | 20 | 20 | | | | |
| Phthalic acid ester B | | | | | | | | |
| Isopentyl propionate | | | | | 5 | 5 | 5 | 10 |
| Isopentyl butyrate | | | | | | | | |
| Butyl benzoate | | | | | | | | |
| Organic gelling agent | | | | | | | | |
| Gelol D | 0.8 | 0.06 | 0.4 | 0.2 | 0.6 | 0.2 | 0.06 | 0.04 |
| Propylene glycol | | | | | | | | |
| Specific gravity adjusting agent | | | | | | | | |
| Aerosil | 0 | 1 | 5 | 10 | 0 | 1 | 5 | 10 |

TABLE D-7

| Example | 7-1 | 7-2 | 7-3 | 7-4 | 7-5 | 7-6 | 7-7 | 7-8 |
|---|---|---|---|---|---|---|---|---|
| Properties | | | | | | | | |
| Specific gravity | | | | | | | | |
| (at 23° C. in constant-temperature chamber) | 1.040 | 1.049 | 1.048 | 1.045 | 1.031 | 1.035 | 1.055 | 1.068 |
| Viscosity (E-type viscometer) | | | | | | | | |
| 15° C. (× 10,000 cP) | 52.4 | 25.6 | 22.6 | 9.4 | 57.0 | 30.1 | 26.4 | 38.5 |
| 25° C. (× 10,000 cP) | 11.3 | 8.6 | 8.1 | 4.8 | 12.3 | 7.2 | 10.8 | 9.7 |
| Performance | | | | | | | | |
| Invertibility (15° C., 1300 G × 5 min) | B | A | A | A | B | A | A | A |
| White turbidity | No | No | No | No | No | No | No | No |
| Evaluation after standing | Good | Good | Good | Good | Good | Good | Good | Good |

TABLE C-8

| Comparative Example | 8-1 | 8-2 | 8-3 | 8-4 |
|---|---|---|---|---|
| (parts by weight) | | | | |
| Cyclopentadiene resin | | | | |
| ECR-327 | 100 | 100 | 100 | 100 |
| Viscosity adjusting agent | | | | |
| Phthalic acid ester A | 5 | 0 | 5 | |
| Phthalic acid ester B | | | | |
| Isopentyl propionate | | | | 5 |
| Isopentyl butyrate | | | | |
| Butyl benzoate | | | | |
| Organic gelling agent | | | | |
| Gelol D | | 0.08 | 0 | 0 |
| Propylene glycol | 2 | | | |
| Specific gravity adjusting agent | | | | |
| Aerosil | 3 | 3 | 3 | 3 |

TABLE D-8

| Comparative Example | 8-1 | 8-2 | 8-3 | 8-4 |
|---|---|---|---|---|
| Properties | | | | |
| Specific gravity | | | | |
| (at 23° C. in constant-temperature chamber) | 1.042 | 1.046 | 1.042 | 1.036 |
| Viscosity (E-type viscometer) | | | | |
| 15° C. (× 10,000 cP) | 46.3 | >100 | 32.7 | 24.1 |
| 25° C. (× 10,000 cP) | 11.1 | 17.2 | 10.3 | 8.2 |
| Performance | | | | |
| Invertibility (15° C., 1300 G × 5 min) | A | C | A | A |
| White turbidity | Yes | No | No | No |
| Evaluation after standing | Good | Good | EF* | EF* |

*EF = excessive flow

TABLE C-9

| | (parts by weight) | | | |
|---|---|---|---|---|
| Comparative Example | 9-1 | 9-2 | 9-3 | 9-4 |
| Cyclopentadiene resin | | | | |
| Hydrogenated Quintone-1 | 100 | 100 | 100 | 100 |
| Viscosity adjusting agent | | | | |
| Phthalic acid ester A | 5 | 0 | 5 | |
| Phthalic acid ester B | | | | |
| Isopentyl propionate | | | | 5 |
| Isopentyl butyrate | | | | |
| Butyl benzoate | | | | |
| Organic gelling agent | | | | |
| Gelol D | | 0.08 | 0 | 0 |
| Propylene glycol | 2 | | | |
| Specific gravity adjusting agent | | | | |
| Aerosil | 3 | 3 | 3 | 3 |

TABLE D-9

| Comparative Example | 9-1 | 9-2 | 9-3 | 9-4 |
|---|---|---|---|---|
| Properties | | | | |
| Specific gravity | | | | |
| (at 23° C. in constant-temperature chamber) | 1.042 | 1.046 | 1.042 | 1.036 |
| Viscosity (E-type viscometer) | | | | |
| 15° C. (× 10,000 cP) | 27.4 | >100 | 19.5 | 14.4 |
| 25° C. (× 10,000 cP) | 6.6 | 10.1 | 6.2 | 4.8 |
| Performance | | | | |
| Invertibility (15° C., 1300 G × 5 min) | A | C | A | A |
| White turbidity | Yes | No | No | No |
| Evaluation after standing | Good | Good | EF* | EF* |

*EF = excessive flow

The tables reveal the following. The separating compositions of Examples 1-1 to 1-14, 2-1 to 2-14, 3-1 to 3-14, 4-1 to 4-14, 5-1 to 5-5, 6-1 to 6-2 and 7-1 to 7-8 formed satisfactory separating layers, were free from white turbidity due to water absorption and remained satisfactory despite standing.

As shown in Tables C-1 and D-1, however, the separating compositions of Comparative Examples 1-1 and 1-3 exhibited poor invertibility due to the presence of a smaller amount of viscosity adjusting agent, and the compositions of Comparative Examples 1-2 and 1-4 underwent phase separation when tested by standing owing to the presence of an excess of the viscosity adjusting agent.

Tables C-2 and D-2 show that the use of a lesser amount of the organic gelling agent in the compositions of Comparative Exhales 2-1 and 2-3 resulted in an excessive flow when checked by standing, and that an excess of the organic gelling agent present in the compositions of Comparative Examples 2-2 and 2-4 caused an excessive rise in viscosity, giving poor invertibility.

As shown in Tables C-3 and D-3, the compositions of Comparative Examples 3-1 and 3-3 were low in invertibility due to the use of a reduced amount of viscosity adjusting agent, and the compositions of Comparative Examples 3-2 and 3-4 exhibited phase separation during standing due to an excess of viscosity adjusting agent.

Tables C-4 and D-4 indicate that the use of a reduced amount of organic gelling agent in the compositions of Comparative Examples 4-1 and 4-3 resulted in an excessive flow during standing, and that an excess of organic gelling agent present in the compositions of Comparative Examples 4-2 and 4-4 caused an excessive rise in viscosity to result in low invertibility.

Tables C-8 and D-8 indicate that the use of propylene glycol as the organic gelling agent in the composition of Comparative Example 8-1 produced white turbidity in the composition due to water absorption. It is also seen that the absence of viscosity adjusting agent in the composition of Comparative Example 8-2 resulted in low invertibility at 15° C., and that the absence of organic gelling agent in the compositions of Comparative Examples 8-3 and 8-4 caused an excessive flow during standing.

As apparent from Tables C-9 and D-9, propylene glycol used as the organic gelling agent in the composition of Comparative Example 9-1 caused white turbidity due to water absorption, the absence of viscosity adjusting agent in the composition of Comparative Example 9-2 resulted in low invertibility at 15° C., and the absence of organic gelling agent in the compositions of Comparative Examples 9-3 and 9-4 led to an excessive flow during standing.

Examples 10-1 to 10-6, and
Comparative Example 11

Separating compositions were prepared from specified amounts of the following materials.

Hydrogenated cyclopentadiene resin: 100 parts by weight of ECR-327, product of Exxon Chemical Co., Ltd., having the properties listed in Table A.

Viscosity adjusting agent: 5 parts by weight of phthalic acid ester B (brand name: PL-200, product of Mitsubishi Gas Chemical Co., Inc.).

Organic gelling agent: 0.2 part by weight of Gelol D which is dibenzylidene sorbitol manufactured by Shin-nihon Rika Co., Ltd. (Gelol D was used as dissolved in dimethyl sulfoxide in the form of 20 wt. % solution.)

Specific gravity adjusting agent: 3 parts by weight of finely divided silica, i.e., Aerosil, product of Nippon Aerosil Co., Ltd. (5 to 20 nm in primary particle size, about 7 nm in mean primary particle size).

Gamma-ray stabilizer: Phenolic antioxidant: n-octadecyl-3-(4'-hydroxy-3',5'-di-tert-butylphenyl) propionate (brand name): ADK STAB AO-50, product of Asahi Denka Kogyo K.K.).

Photostabilizer: bis(2,2,6,6-tetramethyl-4-piperidyl) sebacate (brand name: ADK STAB LA-77, product of Asahi Denka Kogyo K.K.).

Phosphite antioxidant: 4,4'-butylidene-bis(3-methyl-6-tert-butylphenyl-di-tridecyl)phosphite (brand name: ADK STAB 260, product of Asahi Denka Kogyo K.K.).

The gamma-ray stabilizer was used in the form of a 58 wt. % solution prepared by dissolving a mixture of the above three components in N-methylpyrrolidone.

These gamma-ray stabilizer components were admixed in the proportions listed in Table E with 100 parts by weight of ECR-327, 5 parts by weight of phthalic acid ester B, 0.2 part by weight of Gelol D and 3 parts by weight of Aerosil, and the resulting mixture was kneaded in a vaccum for 80 minutes to prepare each serum or plasma separating composition.

The compositions obtained were checked for bubbling resulting from gamma-ray irradiation, invertibility and white turbidity due to water absorption.

Table E shows the results.

The following checking procedures were used.

First, 1.2 g of the composition was placed into commercial 10-ml borosilicate glass tubes to prepare blood testing containers for use as samples for the evaluation of properties.

To check the composition for bubbling due to gamma-ray irradiation, the samples were irradiated with gamma rays at a dose of 2.5 Mrads (2.6 to 2.8 Mrads as actually measured) or 5.0 Mrads (5.2 to 5.6 Mrads as actually measured using cobalt-60 as a radiation source.

The samples were then checked for bubbling with the unaided eye, and the ratio of the number of samples free of bubbling to the total number of samples (100 samples) was calculated as a bubbling inhibition ratio. (Although medical instruments can be fully sterilized with gamma rays usually when irradiated at a dose of 2.5 Mrads, the composition was tested also by 5.0-Mrad irradiated in view of irregularities involved in irradiation and likelihood of re-sterilization.)

The composition was checked for invertibility and white turbidity in the same manner as in the foregoing examples.

The evaluation symbols A, B and C in Table E have the same meaning as already stated.

TABLE E

| | Ex. 10-1 | Ex. 10-2 | Ex. 10-3 | Ex. 10-4 | Ex. 10-5 | Ex. 10-6 | Comp. Ex. 11 |
|---|---|---|---|---|---|---|---|
| Gamma-ray stabilizer (parts by wt.) | | | | | | | |
| AO-50 | 0 | 0.05 | 0.1 | 0.15 | 0.2 | 0.5 | 0.75 |
| LA-77 | 0 | 0.25 | 0.5 | 0.75 | 1.0 | 2.5 | 3.75 |
| 260 | 0 | 0.25 | 0.5 | 0.75 | 1.0 | 2.5 | 3.75 |
| Solvent (parts by wt.) | | | | | | | |
| N-methyl-pyrrolidone | 0 | 0.4 | 0.8 | 1.2 | 1.6 | 4.0 | 6.0 |
| Bubbling inhibition ratio (%) | | | | | | | |
| 2.5-Mrad irradiation | 35 | 40 | 80 | 100 | 100 | 100 | 100 |
| 5.0-Mrad irradiation | 15 | 20 | 30 | 50 | 100 | 100 | 100 |
| Invertibility | A | A | A | A | A | A | A |
| White turbidity | No | No | No | No | No | No | Yes |

As will be apparent from the above table, the separating compositions of Examples and Comparative Example proved fully satisfactory in invertibility.

The compositions of Examples 10-1, 10-2 and 10-3 exhibited no turbidity due to water absorption but bubbled when irridiated with 2.4-Mrad and 5.0-Mrad gamma rays.

The composition of Example 10-4 exhibited no turbidity due to water absorption, remained free of bubbling when exposed to 2.5-Mrad gamma rays but bubbled when irradiated at 5.0 Mrads.

The compositions of Examples 10-5 and 10-6 exhibited no turbidity due to water absorption and remained free of bubbling when irradiated with 2.5-Mrad and 5.0-Mrad gamma rays.

Accordingly, the separating compositions of Examples 10-1, 10-2 and 10-3 fulfill the foregoing first object, while those of examples 10-4, 10-5 and 10-6 accomplish both the first and second objects.

In contrast, the composition of Comparative Example 11 become turbid owing to the presence of an increased amount of N-methylpyrrolidone which entailed water absorption although remaining unbubbled despite 2.5-Mrad and 5.0-Mrad irradiation.

Examples 12-1 to 12-4

Exactly the same procedures as in Examples 2-5, 2-6, 2-7 and 2-8 were repeated except that each of serum or plasma separating compositions was accommodated in a 10-ml polyethylene terephthalate resin tube in place of the 10-ml borosilicate glass tube.

The compositions accommodated in the resin tubes exhibited exactly the same properties (invertibility, white turbidity due to water absorption and evaluation after standing) as the corresponding compositions placed in the glass tubes in Examples 2-5, 2-6, 2-7 and 2-8.

Examples 13-1 to 13-6

Exactly the same procedures as in Examples 10-1 to 10-6 were repeated except that each of the serum or plasma separating compositions was accommodated in a 10-ml polyethylene terephthalate resin tube in place of the 10-ml borosilicate glass tube.

The composition accommodated in the resin tubes exhibited exactly the same properties (bubbling inhibition ratio, invertibility and white turbidity due to water absorption) as the corresponding compositions placed in the glass tubes in Examples 10-1 to 10-6.

What we claim is:

1. A serum or plasma separating composition comprising a cyclopentadiene resin, a viscosity reducing agent and an organic gelling agent, the cyclopentadiene resin being a liquid resin at a temperature of 25° C., the viscosity reducing agent being a liquid ester prepared by reacting an alcohol with an acid selected from the group consisting of propionic acid, butyric acid, benzoic acid and phthalic acid, the organic gelling agent being a condensation product of sorbitol and an aromatic aldehyde, the composition containing 0.8 to 25 parts by weight of the viscosity reducing agent and 0.03 to 0.9 part by weight of the organic gelling agent per 100 parts by weight of the cyclopentadiene resin.

2. A separating composition as defined in claim 1 wherein the cyclopentadiene resin has a number average molecular weight of 100 to 300 as determined by polystyrene calibration of the result of gel permeation chromatography.

3. A separating composition as defined in claim 1 wherein the cyclopentadiene resin is a hydrogenated resin having a bromine value of up to 5.0 (g $Br_2$/100 g) as determined by the method prescribed in JIS K 2543.

4. A separating composition as defined in claim 1 wherein the viscosity reducing agent is di(2-ethylhexyl)phthalate.

5. A separating composition as defined in claim 1 wherein the viscosity reducing agent is a phthalic acid ester obtained from a mixture of alcohols having a high straight-chain ratio with 9 to 11 carbon atoms.

6. A separating composition as defined in claim 1 wherein the viscosity reducing agent is isopentyl butyrate.

7. A separating composition as defined in claim 1 wherein the viscosity reducing agent is isopentyl propionate.

8. A separating composition as defined in claim 1 wherein the viscosity reducing agent is butyl benzoate.

9. A separating composition as defined in claim 1 wherein the viscosity reducing agent is present in a proportion of 3 to 20 parts by weight per 100 parts by weight of the cyclopentadiene resin.

10. A separating composition as defined in claim 1 wherein the organic gelling agent is dibenzylidene sorbitol.

11. A separating composition as defined in claim 1 which is obtained by incorporating the organic gelling agent in the form of a solution thereof in dimethyl sulfoxide.

12. A separating composition as defined in claim 1 wherein the organic gelling agent is present in a proportion of 0.04 to 0.4 part by weight per 100 parts by weight of the cyclopentadiene resin.

13. A serum or plasma separating composition comprising a cyclopentadiene resin, a viscosity reducing agent, an organic gelling agent and a gamma-ray stabilizer, the cyclopentadiene resin being a liquid resin at a temperature of 25° C., the viscosity reducing agent being a liquid ester prepared by reacting an alcohol with an acid selected from the group consisting of propionic acid, butyric acid, benzoic acid and phthalic acid, the organic gelling agent being a condensation product of sorbitol and an aromatic aldehyde, the gamma-ray stabilizer being a mixture of a phenolic antioxidant, a photostabilizer and a phosphite antioxidant, the composition containing 0.8 to 25 parts by weight of the viscosity reducing agent, 0.03 to 0.9 part by weight of the organic gelling agent and 1.32 to 7.7 parts by weight of the gamma-ray stabilizer per 100 parts by weight of the cyclopentadiene resin.

14. A separating composition as defined in claim 13 wherein the phenolic antioxidant is n-octadecyl-3-(4'-hydroxy-3',5'-di-tert-butylphenyl)propionate, the photostabilizer is bis(2,2,6,6-tetramethyl-4-piperidyl)sebacate and the phosphite antioxidant is 4,4'-butylidene-bis(3-methyl-6-tert-butylphenyl-di-tridecyl)phosphite, the composition containing 0.12 to 0.7 part by weight of the phenolic antioxidant, 0.6 to 3.5 parts by weight of the photostabilizer and 0.6 to 3.5 parts by weight of the phosphite antioxidant per 100 parts by weight of the cyclopentadiene resin.

15. A separating composition as defined in claim 1 which further comprises up to 50 parts by weight of a specific gravity adjusting agent per 100 parts by weight of the cyclopentadiene resin.

16. A separating composition as defined in claim 15 wherein the specific gravity adjusting agent is silica.

17. A blood testing container having contained therein a serum or plasma separating composition as defined in claim 1.

18. A blood testing container having contained therein a serum or plasma separating composition as defined in claim 13.

19. A blood testing container having contained therein a serum or plasma separating composition as defined in claim 14.

* * * * *